United States Patent [19]

Yoshimura et al.

[11] 3,985,869

[45] Oct. 12, 1976

[54] DENTAL CARIES-INDUCING MICROORGANISM CELLS LYTIC ENZYME

[75] Inventors: Yoshio Yoshimura, Nishinomiya; Kanae Yokogawa, Nara; Shigeo Kawata, Kobe, all of Japan

[73] Assignee: Dainippon Pharmaceutical Co., Ltd., Dosho, Japan

[22] Filed: Apr. 22, 1975

[21] Appl. No.: 570,369

Related U.S. Application Data

[60] Division of Ser. No. 270,821, July 11, 1972, Pat. No. 3,929,579, which is a continuation-in-part of Ser. No. 180,711, Sept. 15, 1971, abandoned, which is a continuation-in-part of Ser. No. 68,944, Sept. 2, 1970, abandoned, which is a continuation-in-part of Ser. No. 26,010, April 6, 1970, abandoned.

[30] Foreign Application Priority Data

June 7, 1969 Japan.............................. 44-45307
May 28, 1970 Japan.............................. 45-46494

[52] U.S. Cl.................................. 424/50; 424/48; 424/94
[51] Int. Cl.² .................... A61K 7/28; A61K 37/48
[58] Field of Search ................................ 424/49–58, 424/94

[56] References Cited

UNITED STATES PATENTS

| | | | |
|---|---|---|---|
| 3,590,121 | 6/1971 | Schiff et al. | 424/50 |
| 3,696,191 | 10/1972 | Weeks | 424/50 |
| 3,751,561 | 8/1973 | Wildi et al. | 424/50 |

OTHER PUBLICATIONS

Yasumatsu et al., *Agr. Biol. Chem.*, vol. 29, No. 7, pp. 665–671, 1964.

*Primary Examiner*—Shep K. Rose
*Attorney, Agent, or Firm*—Stevens, Davis, Miller & Mosher

[57] ABSTRACT

An enzyme being capable of lysing cells of dental caries-inducing microorganisms and a method for producing the same by cultivating a microorganism belonging to the genus Streptomyces, especially wild type strains of *Streptomyces diastatochromogenes*, *Streptomyces farinosus*, *Streptomyces globisporus* and *Streptomyces griseus* var. H-402, compositions for preventing and treating dental caries containing the said enzyme and methods for preventing and treating dental caries.

6 Claims, 7 Drawing Figures

1. ACETATE BUFFER  3. PHOSPHATE BUFFER
2. TRIS-MALEATE BUFFER  4. TRIS BUFFER
(CONCENTRATION OF BUFFER SOLUTION: 0.025 M)

FIG. 1

1. ACETATE BUFFER  3. TRIS BUFFER
2. PHOSPHATE BUFFER
(CONCENTRATION OF BUFFER SOLUTION: 0.025 M)

FIG. 2

1. ACETATE BUFFER   3. TRIS BUFFER
2. PHOSPHATE BUFFER
(CONCENTRATION OF BUFFER SOLUTION: 0.025M)

FIG. 3

1. ACETATE BUFFER   3. TRIS BUFFER
2. PHOSPHATE BUFFER
(CONCENTRATION OF BUFFER SOLUTION: 0.025M)

——— = CELL-LYTIC CURVE IN FREEZE-DRIED STREPTOCOCCUS (BHT)
---- = CELL-LYTIC CURVE IN HEAT-TREATED STREPTOCOCCUS (BHT)

1 AND 5 = ACETATE BUFFER
2 AND 6 = TRIS BUFFER
3 AND 7 = PHOSPHATE BUFFER
4 AND 8 = TRIS-MALEATE BUFFER

FIG. 6

1 = CELL-LYTIC CURVE IN FREEZE-DRIED STREPTOCOCCUS (BHT)
2 = CELL-LYTIC CURVE IN HEAT-TREATED STREPTOCOCCUS (BHT)

FIG. 7

DENTAL CARIES-INDUCING MICROORGANISM CELLS LYTIC ENZYME

This is a division of application Ser. No. 270,821, filed July 11, 1972, now U.S. Pat. No. 3,929,579 which is a continuation-in-part of application Ser. No. 180,711, filed on Sept. 15, 1971 now abandoned, which, in turn, is a continuation-in-part of application Ser. No. 68,944, filed on Sept. 2, 1970 now abandoned, which, in turn, is a continuation-in-part of application Ser. No. 26,010, filed on Apr. 6, 1970 now abandoned.

The present invention relates to an enzyme being capable of lysing cells of microorganisms and a method for producing the same and new compositions for preventing and treating dental caries and methods for preventing and treating dental caries.

More particularly, it relates to an enzyme being capable of lysing cells of dental caries-inducing microorganisms such as cariogenic streptococci and lactobacillus and a method for producing the same by cultivating a microorganism belonging to the genus Streptomyces, also to compositions for preventing and treating dental caries containing the said enzyme and methods for preventing and treating dental caries.

Since it had been pointed out by Miller in 1890 that dental caries might be induced by bacteria, causes of dental caries have been studied from a microbiological viewpoint by investigators. In 1960 Fitzgerald and Keyes have reported that an experimental caries was induced by streptococci in hamster (The Journal of the American Dental Association, Vol. 61, pages 9 – 19, 1960). Recently, it has been reported that dental plaque or caries development could be prevented by degrading microbially produced dextran and removing away the dental plaque by using an enzyme "dextranase" (Fitzgerald et al; Archives Oral Biology, Vol. 13, pages 125 – 128, 1968 and the Journal of the American Dental Association, Vol. 76, pages 301 – 304, 1968). Furthermore, it has been attempted to control the growth of dental caries-inducing bacteria by using of various compounds and medicaments and thereby to prevent or treat the dental caries. However, it has never been attempted to lyse and kill out the bacteria by using enzyme.

There has been studied a method of preventing and treating dental caries by means of attacking in direct against the dental caries-inducing microorganisms and thereby controlling their growth. It has been found that the dental caries-inducing microorganisms such as cariogenic streptococci and lactobacillus are a kind of microorganism being difficult to be lysed and that they could be lysed by neither egg white lysozyme which has been known as a bacteria cell-lytic enzyme nor enzymes produced by type culture of several kinds of microorganisms, i.e. type culture of Streptomyces albus or Streptomyces griseus, or a strain belonging to the genus Flavobacterium which has been known as a microorganism being able to produce bacteria cell-lytic enzymes.

As a result of a screening of many kinds of microorganisms existing in soil or sewage for the purpose of finding an enzyme being capable of lysing cells of dental caries-inducing microorganisms, it has now been found that some strains belonging to the genus Streptomyces produce an enzyme strongly lysing the said dental caries-inducing microorganisms.

One object of the present invention is to provide an enzyme being capable of lysing cells of dental caries-inducing microorganisms.

Another object of the present invention is to provide a method for producing an enzyme capable of lysing cells of dental caries-inducing microorganisms.

A further object of the present invention is to provide compositions for preventing and treating dental caries containing the aforesaid enzyme.

A still further object of the present invention is to provide methods for preventing and treating dental caries by the application of the aforesaid compositions.

These and other objects will more clearly appear hereinafter.

Among the strains producing an enzyme capable of lysing cells of dental caries-inducing microorganisms isolated by the present inventors, the representatives are deposited with American Type Culture Collection, U.S.A. (hereinafter, referred to as ATCC) and with Fermentation Research Institute, Agency of Industrial Science and Technology, Japan (hereinafter, referred to as FERM). They are S-1 strain (ATCC No. 21481: FERM-P No. 326), H-191 strain (ATCC No. 21482: FERM-P No. 327), H-402 strain (ATCC No. 21483: FERM-P No. 328) and B-1829 strain (ATCC No. 21553: FERM-P No. 596).

The morphological, cultural and physiological characteristics of these strains are set forth in the following Table I.

TABLE I

|  |  | S-1 strain | H-191 strain | H-402 strain | B-1829 strain |
|---|---|---|---|---|---|
| Microscopic observation of aerial mycelium | | Long straight; sporophores no spirals, no whorls; spores spherical | Aerial mycelium powdery white; sporophores straight or wavy, no whorls; spores cylindrical | Aerial mycelium branches in cluster; sporophores straight no spirals, no whorls; spores spherical | Aerial mycelium straight or wavy; no spirals, no whorls; spores spherical, 0.4 – 0.6 $\mu$ in size |
| a) Cultural properties on various media | | | | | |
| 1) | Czapek's agar | Abundant growth brown; cottony gray aerial mycelium; soluble pigment reddish brown | Abundant growth light green; powdery grayish white aerial mycelium; no soluble pigment | Very scant thin surface growth; powdery white to yellow aerial mycelium; no soluble pigment | Scanty growth; aerial mycelium light brown; no soluble pigment |
| 2) | Glucose asparagine agar | Abundant growth reddish brown; cottony aerial mycelium; media turning from white to gray; soluble | Moderate growth light green; powdery white aerial mycelium; no soluble pigment | Good growth, folding, spreading olive-buff to cream; thin, powdery white cream to gray | Abundant growth light ivory; powdery, cream-colored aerial mycelium; soluble pigment faint |

TABLE I-continued

|  |  | S-1 strain | H-191 strain | H-402 strain | B-1829 strain |
|---|---|---|---|---|---|
|  |  | pigment reddish brown |  | olive-buff aerial mycelium; no soluble pigment | yellowish brown |
| 3) | Starch agar | Abundant growth brown; cottony aerial mycelium | Moderate growth light grayish green; powdery white aerial mycelium; no soluble pigment | Very scanty growth, reverse yellow dull; thin, powdery gray aerial mycelium; no soluble pigment | Moderate growth faint cocoa brown; thick, white aerial mycelium; soluble pigment faint brown |
| 4) | Calcium malate glycerin agar | Abundant growth reddish brown; powdery grayish white aerial mycelium; soluble pigment light reddish brown | Moderate growth light green powdery white aerial mycelium; no soluble pigment | Abundant growth, spreading light yellow; powdery white to yellow aerial mycelium; soluble pigment faint yellow | Abundant growth cream-colored; powdery, cream-colored aerial mycelium; soluble pigment faint brown |
| 5) | Skim-milk | Surface ring; no aerial mycelium; coagulation; no peptonization; soluble pigment light red | Surface ring; no aerial mycelium; coagulation; no peptonization; no soluble pigment | Surface ring; aerial mycelium creamy green, coagulation with rapid peptonization, becoming alkaline |  |
| 6) | Potato | Abundant growth wrinkled; turning from yellow to dark brown; grayish white aerial mycelium; soluble pigment dark brown | Abundant growth wrinkled light brown; grayish white aerial mycelium; soluble pigment grayish white | Excellent growth wrinkled turning to brown; aerial mycelium gray to olive-buff | Thick, mossy growth wrinkled; mossy, light gray aerial mycelium; soluble pigment brown |
| 7) | Gelatin stab | Growth on surface dark brown; no aerial mycelium; soluble pigment dark brown | Growth on surface; no aerial mycelium; no soluble pigment | Faint cream-colored; rapid liquefaction; aerial mycelium white to gray; no soluble pigment | Very scanty growth; scanty, white aerial mycelium; no soluble pigment |
| 8) | Tyrosine agar | Abundant growth |  | Scanty growth, reverse yellow to light brown; aerial mycelium faint brown; no soluble pigment | Abundant growth faint orange; powdery, cream-colored aerial mycelium; soluble pigment faint yellow |
| 9) | Nutrient agar | Abundant growth reddish brown; cottony gray aerial mycelium; soluble pigment reddish brown | Moderate growth dark green; powdery grayish white aerial mycelium; no soluble pigment | Abundant growth, reverse white to brown; thin, powdery aerial mycelium light gray; soluble pigment light brown | Abundant growth cream-colored; scanty, white aerial mycelium; soluble pigment faint brown |
| 10) | Glucose nutrient agar |  |  |  | Abundant growth mustard-like golden; thick, powdery cream-colored aerial mycelium; soluble pigment faint brown |
| 11) | Glucose peptone agar |  |  |  | Thick growth faint golden; scanty, white aerial mycelium; soluble pigment faint brown |
| 12) | Litmus milk |  |  |  | Growth with circular or thin membranous surface, light yellow; white aerial mycelium; no soluble pigment |
| 13) | Yeast extract-malt extract agar |  |  |  | Abundant growth bright golden; thick, cream-colored aerial mycelium; soluble pigment light brown |
| 14) | Oatmeal agar |  |  |  | Moderate growth faint yellowish brown; thick, white aerial mycelium; |
|  | soluble pigment |  |  |  | light brown |
| 15) | Glycerine-asparagine agar |  |  |  | Abundant growth faint yellowish brown; thick, powdery, cream-colored aerial mycelium; soluble pigment faint yellow |
| b) | Physiological properties |  |  |  |  |
| 1) | Gelatin | Positive | Positive | Positive | Positive |

TABLE I-continued

|  |  | S-1 strain | H-191 strain | H-402 strain | B-1829 strain |
|---|---|---|---|---|---|
|  | liquefaction |  |  |  |  |
| 2) | Starch hydrolysis | Positive | Positive | Positive | Positive |
| 3) | Reduction of nitrate | Positive | Negative | Positive | Positive |
| 4) | Cellulose decomposition | Negative | Negative | Negative |  |
| 5) | Tyrosinase reaction |  |  |  | Negative |
| 6) | Litmus milk |  |  |  | Peptonization |
| 7) | Pigment producing reaction |  |  |  | Negative |
| 8) | Optimum temperature | 20 – 30° C. | 20 – 30° C. | 20 – 30° C. | 20 – 30° C. |
| 9) | Optimum pH | 6.5 – 7.5 Aerobic | 6.5 – 7.5 Aerobic | 6.5 – 7.5 Aerobic | 6.5 – 7.5 Aerobic |
| c) | Utilization of saccharide |  |  |  |  |
|  | Rhamnose | – | – | – | ± |
|  | Xylose | ± | ± | + | + |
|  | Lactose | ++ | ± | + | + |
|  | Sucrose | + | + | ± | ± |
|  | Arabinose | ++ | ++ | ++ | + |
|  | Raffinose | – | – | – | ± |
|  | Fructose | – | ++ | + | + |
|  | Mannose | – | ++ | ++ | + |
|  | Inositol | – | – | – | ± |
|  | Galactose | ++ | ++ | ++ |  |
|  | Sorbitol | – | – | – |  |
|  | Glucose | ++ | ++ | ++ | + |
|  | Mannitol |  |  | ++ | + |
|  | Salicin |  |  |  | + |
|  | Cellulose |  |  |  | – |

On the basis of these morphological, cultural and physiological characteristics the classification of the strains has been determined according to Bergey's Mannual of Determinative Bacteriology 7th Edition and Waksman's The Actinomycetes. Consequently, it seems that S-1 strain, H-191 strain and B-1829 strain should be classified as *Streptomyces diastatochromogenes*, *Streptomyces farinosus* and *Streptomyces globisporus*, respectively. Furthermore, H-402 strain is analogous to *Streptomyces griseus* but slightly distinguished from it in viewpoint of pigment production, i.e. the color in case of H-402 strain is rather yellow, orange or grayish brown than green. Therefore, it seems to be a new species belonging to Streptomyces series and then has been designated as *Streptomyces griseus* var. H-402.

The present enzyme can be produced by cultivation of a microorganism belonging to the genus *Streptomyces*, which can produce an enzyme being capable lysing cells of dental caries-inducing microorganisms, especially a wild type strain of *Streptomyces diastatochromogenes*, a wild type strain of *Streptomyces farinosus*, a wild type strain of *Streptomyces globisporus* or *Streptomyces griseus* var. H-402.

The present enzyme can be also produced by using of mutants of the described microorganisms such as those obtained by natural mutation, or those produced by mutating agent, for example, X-ray irradiation, ultraviolet irradiation, nitrogen mustards, and the like.

According to the present invention, the microorganism belonging to the genus *Streptomyces* is cultivated in a suitable culture medium containing, for example, proper saccharides, nitrogen sources, inorganic salts and further, if necessary, organic stimulants and thereby the desired enzyme is accumulated in the medium.

Saccharides used in the present culture may be, for example, glucose, maltose, malt extract, dextrin, starch, and the like. The nitrogen sources may be, for example, inorganic nitrogen source such as ammonium sulfate, ammonium chloride, ammonium nitrate, sodium nitrate, potassium nitrate, and the like, and organic nitrogen source such as urea, peptone, soybean extract, yeast extract, meat extract, soybean meal, and the like. Inorganic salts may be, for example, sodium chloride, sodium dihydrogen phosphate, potassium dihydrogen phosphate, disodium hydrogen phosphate, dipotassium hydrogen phosphate, magnesium sulfate, ferric sulfate, zinc sulfate, calcium chloride, and the like. Furthermore, organic stimulants may be, for example, vitamins such as vitamin $B_1$ and vitamin $B_2$, peptone, meat extract, corn steep liquor, and the like.

The pH value of the medium may be preferably controlled at 6 – 9, more particularly at 7 – 8 by addition of acids such as hydrochloric acid and acetic acid or bases such as sodium hydroxide, potassium hydroxide and ammonium hydroxide.

The culture can be carried out by conventional culture methods such as stationary culture, shaking culture and submerged culture, preferably by shaking culture, at 20° – 40° C., preferably at 25° – 37° C. The period of the culture is several hours to several ten days, preferably 1 to 10 days.

Thus obtained culture broth containing the desired enzyme can be submitted to isolation, recovery and purification by means of conventional methods generally used for the production of enzymes. For example, the culture broth may be separated by centrifuge and to the resulting supernatant fluid may be added water or buffer solution, such as acetate buffer, phosphate buffer, tris-maleate buffer, tris buffer (tris-HCl buffer), and the like to give an enzyme solution (hereinafter, referred to as broth enzyme solution). Furthermore, the supernatant fluid may be conventionally purified by means of salting out with ammonium sulfate, precipitation by acetone, dialysis and/or phosphoric acid gel, carboxymethyl cellulose or sephadex chromatography, followed by addition of water or buffer solution to give a purified enzyme solution (hereinafter, referred to as purified enzyme solution). And furthermore, these enzyme solutions can be also freeze-dried to give a dried enzyme product. Both enzyme solutions and the dried enzyme product obtained above can be used for the preparation of composition for preventing and treating dental caries of the present invention.

In FIGS. 1 and 6 the broth enzyme solutions were used as the enzyme solution. In FIG. 2 the purified enzyme solutions were used as the enzyme solution.

Figure 1:
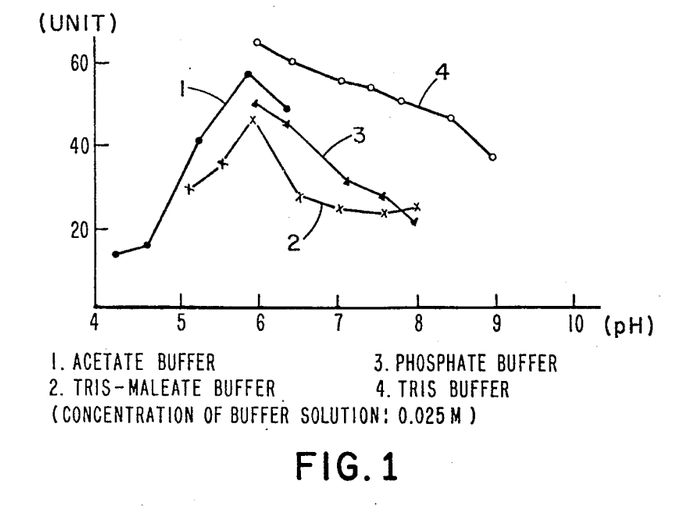
FIGS. 1, 2 and 6 show the relation between pH value and microorganisms cell-lytic activity of the enzyme in case of applying the enzyme solution produced by the present invention to cariogenic streptococci.
Figure 2:
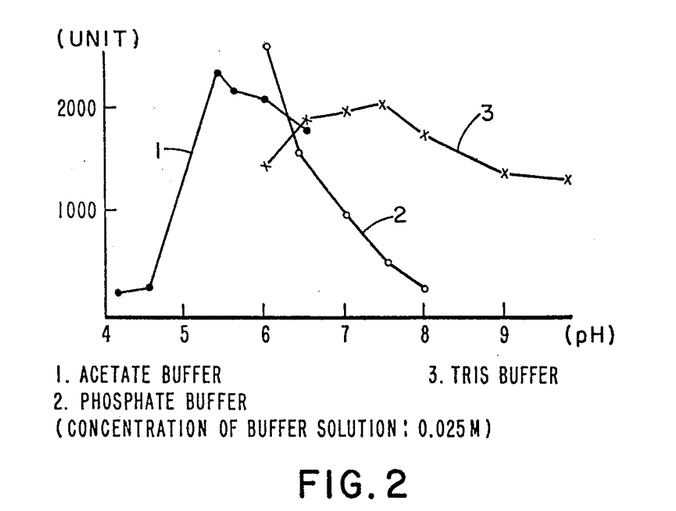
Figure 3:
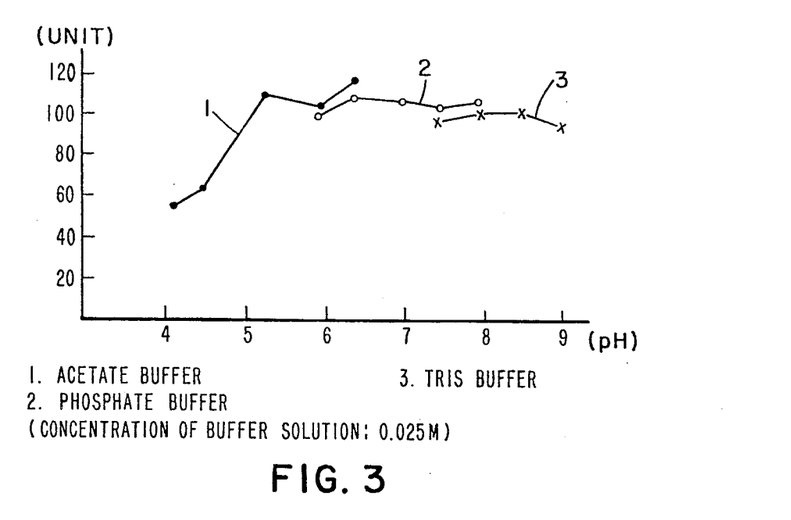
FIGS. 3 and 4 show the stability of the enzyme solution produced by the present invention in which there are compared the activities of the enzyme in case of preserving the enzyme solutions at various pH value for 24 hours at 4° and 37° C., respectively.
Figure 4:
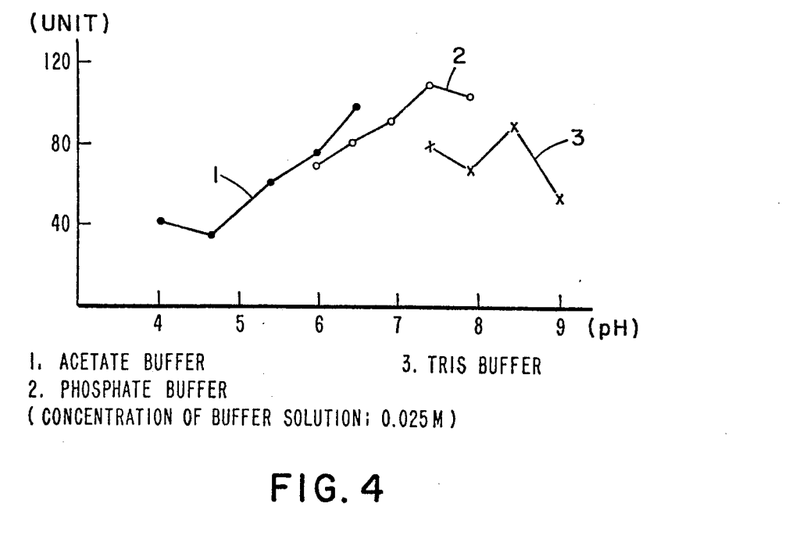
Figure 5:
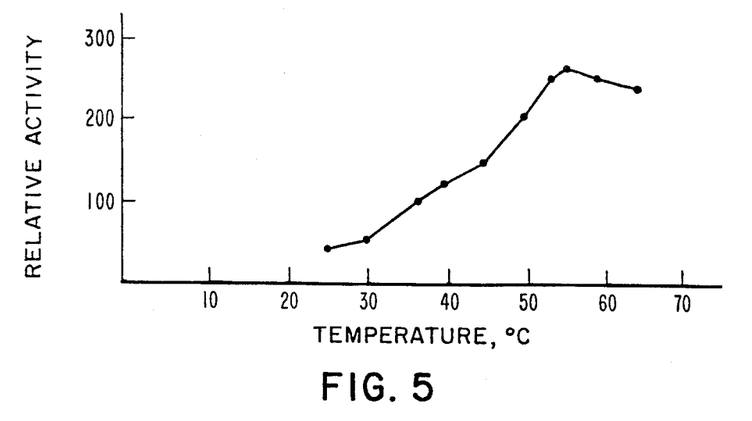
FIG. 5 shows the relation between the temperature and the relative activity of the enzyme solution produced by the present invention, in which the activity of the enzyme solution reacted at 37° C. is used as a standard (100).
Figure 6:
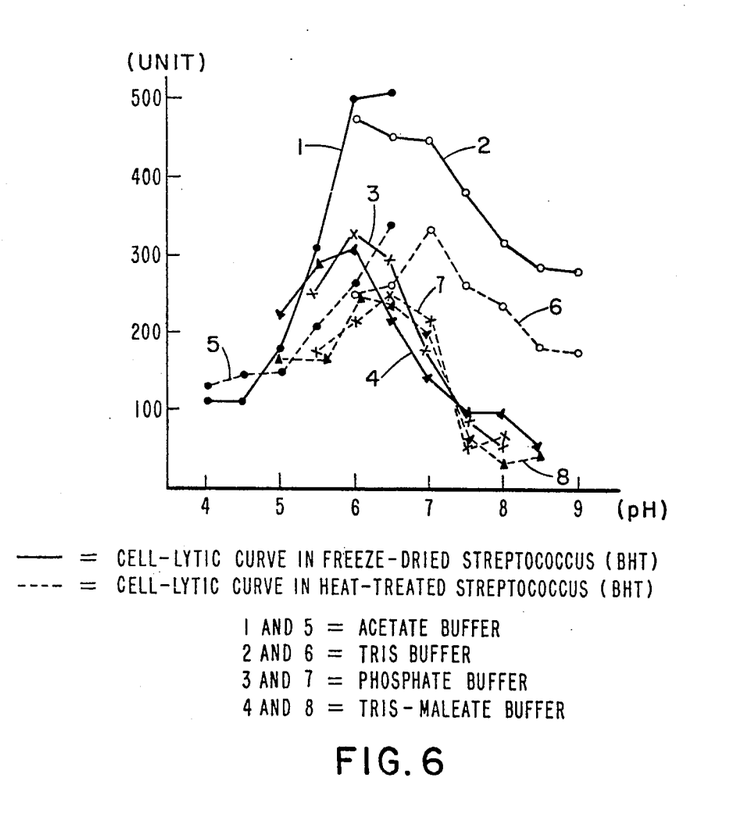
Figure 7:
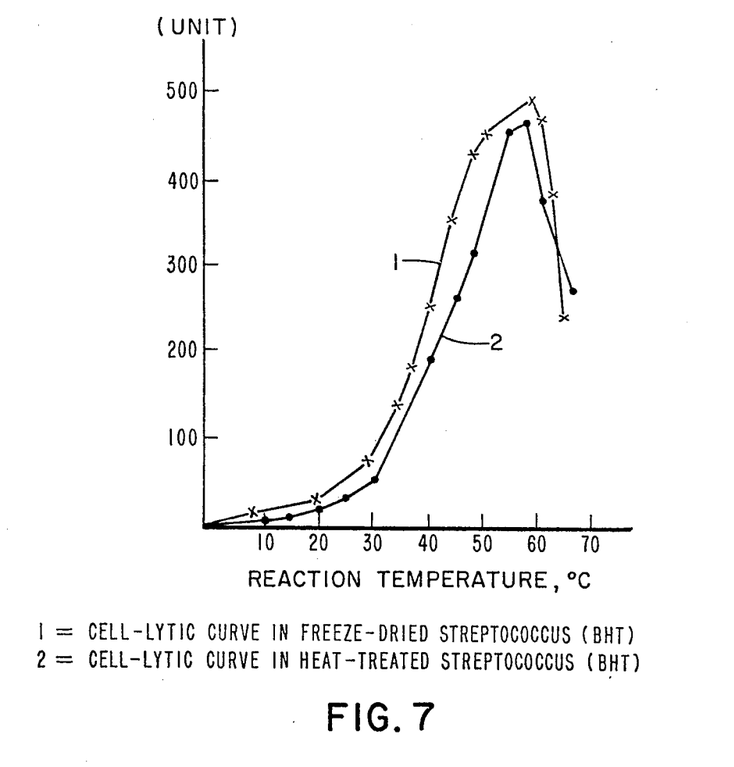
FIG. 7 shows the relation between the temperature and the activity of the enzyme solution produced by the present invention. The enzyme used in FIGS. 1 to 5 is one obtained by cultivation of H-402 strain and that in FIGS. 6 to 7 is one obtained by cultivation of B-1829 strain.

The enzyme produced by the present invention possesses the activity of lysing cells of microorganisms in wide range of pH value, e.g. 5 – 9, as shown in FIGS. 1, 2 and 6. The range of pH value in which the present enzyme is stable and shows superior microorganism cell-lytic activity is approximately 5 – 9, while it is more or less varied according to the temperature for preservation of the enzyme solution, as shown in FIGS. 3 and 4. The optimum temperature is approximately 50° – 60° C., as shown in FIGS. 5 and 7. Besides, the enzyme of the present invention is rather unstable to heat and, for example, it lost the almost activity when it was preserved at 80° C. for 20 minutes in an aqueous solution.

The unit of lytic activity of the present enzyme and the reduction ratio of bacteria cells in turbidity by the present enzyme were calculated according to the following method. 0.4 ml. of a suspension of intact cell or heated cell of microorganisms to be lysed, 2 ml. of an enzyme solution diluted in appropriate concentration and 1.6 ml. of 0.025 M. tris buffer (pH 7.0) were mixed to give total 4.0 ml. The mixture was kept at 37° C. for 5 – 60 minutes to submit to the cell-lytic reaction. Then, the optical density of the reaction mixture was measured at 600 mμ of a photoelectric colorimeter and the unit of lytic activity of the present enzyme and the reduction ratio of bacteria cells in turbidity by the present enzyme were calculated according to the following equations. One unit of activity is defined as that amount of enzyme giving an initial linear decrease in optical density of 0.001 per minute. As a control, 2 ml. of water was used instead of 2 ml. of the enzyme solution.

$$\text{Unit/ml. or mg.} = \frac{(a-b)-(a-c)}{0.001 \cdot t \cdot v} = \frac{c-b}{0.001 \cdot t \cdot v}$$

a: Optical density of the reaction mixture at 600 mμ at zero reaction time b: Optical density of the reaction mixture at 600 mμ after $t$ time c: Optical density of the control solution at 600 mμ after $t$ time t: Reaction time (minute)

v: Amount (ml. or mg.) of actually used original enzyme solution or powder

Reduction ratio =

$$\frac{\begin{array}{c}\text{Optical density of}\\ \text{the control solution}\\ \text{after the reaction}\end{array} - \begin{array}{c}\text{Optical density of}\\ \text{the enzyme solution}\\ \text{after the reaction}\end{array}}{\text{Optical density of the control solution of the reaction}} \times 100$$

The enzyme of the present invention can specifically attack several kinds of dental caries-inducing microorganisms and shows superior microorganism cell-lytic activity. The present enzyme can be, therefore, used for preventing and treating dental caries in humans.

Furthermore, the enzyme is also useful for prevention and treatment of dental plaque which is induced by dental caries-inducing microorganisms and causes of the dental caries. The development of the dental plaque can be subsidiarily controlled as the result of prevention and treatment of dental caries by the present enzyme.

The enzyme of the present invention can be applied to teeth of a human for the purpose of the prevention and treatment of dental caries by conventional methods, conventional types of unit dosages or with conventional carriers. The conventional carriers may be, for example, water, tooth powder, toothpaste, chewing gum, ointment, and the like.

In the preparation of toothpaste and tooth powder containing the present enzyme, conventional vehicles are used unless they give essentially undesired effects to the activity of the enzyme. Suitable water insoluble polishing agent can be contained. The polishing agent may be, for example, dicalcium phosphate, tricalcium phosphate, magnesium carbonate, and the like. These polishing agents will generally comprise a major proportion by weight of the solid ingredients. The content of the polishing agents is preferably about 30 – 60 % by weight of the total composition in toothpaste and 85 – 95 % by weight in tooth powder. The present enzyme is contained in the ratio of about 1 – 5,000 units per gram of the composition.

In the preparation of toothpaste, there may be also added some plasticizers in the mixture of the powdery vehicles to give paste. The plasticizer may be, for example, water, glycerin, sorbitol, propylene glycol, monoglycerin stearate, white petroleum jelly, cetyl alcohol, and the like, or the mixture thereof. It may be preferable to add a gelling agent such as sodium carboxymethyl cellulose, hydroxyethyl cellulose, polyvinyl pyrrolidone, gum tragacanth, and the like in the composition. Furthermore, there may be optionally added other additional components such as flavor, sweeting agent and coloring agent. According to brushing teeth with toothbrush or finger spread with these toothpaste or tooth powder containing the present enzyme, the dental caries-inducing microorganisms on the teeth can be lysed by the enzyme as well as dental plaques are eliminated and the teeth are cleaned up.

The similar effects can be achieved by using a chewing gum containing the present enzyme.

In the preparation of chewing gum containing the present enzyme, there may be used conventional gum base such as chicle resin, polyvinyl acetate, and the like. There may be also added other vehicles such as plasticizer, softener, sugar, flavor and coloring agent. The content of the enzyme may be 1 – 5,000 units per gram of the composition.

Other means for using the present enzyme is a form of ointment. The teeth to be treated are applied with the ointment containing the present enzyme and followed by being rubbed up by finger or a toothbrush. In the preparation of the ointment there may be used conventional vehicles being capable of applying to mouth except one having inhibitory or destructive action on the present enzyme. As an ointment base there may be used materials such as sodium carboxymethyl cellulose, hydroxyethyl cellulose and Plastibase 50 W (dental paste base made by Squibb Co., Ltd.) which can form jelly-like or creamy ointment. The content of the present enzyme may be 1 – 3,000 units per gram.

The present enzyme may be also applied to teeth by means of making a person wash or rinse his mouth with a water containing the enzyme. The water contains about 0.1 – 50 units per milliliter of the present enzyme. It may further contain antibiotics or other sterilizers, and alcohols, flavor, sweetening agent and coloring agent. The washing with the water containing the present enzyme may be also carried out by using a spray.

For mouth wash there may also be used an effervescent granule. In the preparation of the effervescent granule tartaric acid and sodium hydrogen carbonate are used as an effervescent agent and thereto the present enzyme is added in a dose of 1 – 5,000 units per gram of the granule. There may be optionally added other vehicles such as flavor, sweetening agent and coloring agent. The effervescent granule is added to water in a ratio of one gram per 200 to 300 ml. of water when used, and thereby it can be instantaneously dissolved with effervescing. The solution thus obtained is used as a mouth wash.

In these cases, after washing or rinsing the mouth, it may be preferable not to rinse the mouth with clean water since it is desirable to make the enzyme contact with teeth for a long period.

The present enzyme may be also used in a form of chewable tablet or troche. According to chewing or keeping the chewable tablet or troche containing the present enzyme in a mouth the enzyme can be sufficiently in contact with teeth for a long period. In preparation of the chewable tablet or troche containing the present enzyme there may be used conventional vehicles such as mannitol and sorbitol, and other conventional lubricant, sweetening agent, coloring agent, etc. The content of the enzyme may be 1 – 5,000 units in a dose unit.

The present enzyme may be admixed with confectionery such as candy, cake, and the like.

Furthermore, the present enzyme may be administered in admixture with food stuffs or beverage. In this case the enzyme may be mixed with food stuffs or beverage before or after processing thereof.

The method of application of the present enzyme for the purpose of prevention and treatment of dental caries is not limited to the above described methods and many other variants or modifications can be employed. However, in the preparation of the compositions containing the present enzyme it should be noted that heat treatment should be avoided since the present enzyme is unstable to heat and therefore, if necessary, the enzyme should be admixed after the heat treatment.

The present enzyme is unstable to heat as mentioned above and furthermore when the enzyme or a composition thereof is preserved at a room temperature for a long period, the enzyme will be gradually deactivated. Thus, the present enzyme is very unstable and therefore the activity of the enzyme will be lowered in the purification step of raw enzyme obtained by cultivation of the present microorganisms or in the preparation step or the preservation of the compositions containing the enzyme to result in the low yield or the lowering of quality of the product. In view of these disadvantages, it has been studied to find out a stabilizer suitable for stabilizing the present enzyme and then it has been found out that some stabilizers are useful for the purport. Examples of most suitable stabilizer are sucrose, mannose, sorbitol, proline, sorbose, soluble starch and carboxymethyl cellulose and its sodium salt. Among these stabilizers, soluble starch does not show stabilizing effect in aqueous state but is effective in solid state and therefore it can not be used in aqueous compositions but only in solid state compositions. Besides, various grades of carboxymethyl cellulose may be used but it is preferable to be water soluble, especially to be in the form of sodium salt.

To the present enzyme or the enzyme-containing solution obtained by cultivating a microorganisms belonging to the genus Streptomyces are added one or more stabilizers above-mentioned to give a stable enzyme solution or powder.

If necessary, especially in case of using soluble starch as the stabilizer, the solution is freeze-dried to give a stable enzyme powder. Thus obtained stable enzyme solution or powder may be used as mouth wash or rinse after being diluted with or dissolving in water, and further it may be admixed with a carrier to give a stable composition. The stabilizer may be also added in the course of the preparation of enzyme-containing compositions.

These stabilizers may be added alone or in a mixture of two or more kinds of the stabilizers to solution or compositions containing the enzyme in a ratio of about 0.5 part to about 100 parts by weight more preferably about 1 part to about 30 parts by weight in case of sucrose, mannose, sorbitol, proline and sorbose, about 0.5 part to about 80 parts by weight, more preferably about 5 parts to about 10 parts by weight in case of soluble starch and about 0.3 part to about 5 parts by weight, more preferably about 0.7 part to about 2 parts by weight in case of carboxymethyl cellulose or its sodium salt to 1 part by weight of the enzyme.

The quantity of the present enzyme used for the preparation of the present compositions may be variable in accordance with kinds of the compositions and the methods for application as described above, but may be admixed so as to be used 1 – 5,000 units, more preferably 10 – 3,000 units of the enzyme at one time.

The enzyme of the present invention does not show any toxicity or any undesirable side effect even though it would be used for a long time. If the present enzyme would be swallowed, it is deactivated or decomposed in the stomach and converts to harmless amino acids. By contrast, most antibiotics which are generally used for inhibiting various kinds of microorganisms possess wrong effects on intestinal microflora.

The present enzyme has further benefit that there has no enzyme resistant strain of dental caries-inducing microorganisms, while the microorganisms are resistant against most antibiotics.

According to the application of the present enzyme not only cells of th dental caries-inducing microorganisms are lysed and thereby the dental caries is prevented and treated but also the teeth themselves can be made white though the reasons are not elucidated.

The present enzyme can lyse not only dental caries-inducing microorganism cells but also cells of other several kinds of microorganisms, especially gram positive bacteria, particularly those belonging to the genus *Bacillus* and *Lactobacillus*.

The preparation of the present enzyme and the compositions containing the enzyme are set out in the following Examples which are illustrative but not limiting. Unless otherwise noted, the percentages (%) in the compositions of the medium are by weight per volume.

EXAMPLE 1

The isolated H-191 strain was inoculated on a slant agar medium containing 1 % of glucose, 0.2 % of peptone, 0.1 % of yeast extract, 0.1 % of meat extract and 1.5 % of agar and cultivated at 30° C. for 7 days. To the agar slant culture was added 5 ml. of sterilized water and thereby the spores were washed out to give a suspension of spore. 0.5 ml. of thus obtained suspension was inoculated into a 200 ml. Roux flask including 50 ml. of liquid medium (pH 7.5) containing 0.5 % of glucose, 0.5 % of peptone, 0.5 % of sodium chloride, 0.2 % of dipotassium hydrogen phosphate, 0.1 % of magnesium sulfate, 0.004 % of calcium chloride, 0.002 % of ferric sulfate and 0.01 % of zinc sulfate and submitted to stationary culture at 30° C. for 7 days. The obtained culture broth was separated by centrifuge and the resulting supernatant fluid was diluted with distilled water to give an enzyme solution of ten times by volume on which the unit was calculated.

Separately, several kinds of cariogenic streptococcus to be lysed, each 3 – 4 platinum loops were inoculated into a 200 ml. flask including 190 ml. of liquid medium (pH 7.4) containing 2 % of glucose, 1 % of peptone, 1 % of meat extract, 0.5 % of sodium chloride, 0.2 % of yeast extract, 1 % of sodium acetate and $1 \times 10^{-4}$ M. manganese sulfate and submitted to stationary culture at 37° C. for 2 days. The produced cells; were harvested by centrifuge and washed with water twice. The harvested cells were dispersed into 10 ml. of distilled water and sterilized by heating at 100° C. for 20 minutes. The sterilized dispersion was used as a sample to be tested.

To 0.4 ml. of the sample to be tested were added 2 ml. of the enzyme solution obtained above and 1.6 ml. of 0.025 M. acetate buffer (pH 6.0) to give total 4 ml. The mixture was reacted at 37° C. for several ten minutes. The optical density of the reaction mixture at 600 m$\mu$ of a photoelectric colorimeter was measured and then the reduction ratio of the microorganisms to be lysed was calculated in accordance with the equation described above. The results are as shown in Table II.

TABLE II

| Microorganisms to be lysed | Reduction ratio (%) | |
|---|---|---|
| | 10 minutes | 20 minutes |
| Cariogenic streptococcus (AHT) | 34 | 68 |
| Cariogenic streptococcus (BHT) | 36 | 70 |
| Cariogenic | | |

TABLE II-continued

| Microorganisms to be lysed | Reduction ratio (%) | |
|---|---|---|
| | 10 minutes | 20 minutes |
| streptococcus (HS-6) | 38 | 72 |
| Cariogenic streptococcus (K-1-R) | 32 | 67 |
| Cariogenic streptococcus (FA-1) | 36 | 71 |

EXAMPLE 2

The isolated H-402 strain was cultivated in the same manner as described in Example 1 to obtain an enzyme solution. On the other hand, intact cell of cariogenic streptococcus (BHT) was cultivated in the same manner as described in Example 1 to obtain a sample to be tested.

By using these enzyme solution and sample to be tested, the cell-lytic reaction was carried out in the same manner as described in Example 1 and the reduction ratio of the microorganisms to be lysed was calculated as well. The results are shown in Table III.

TABLE III

| Volume of enzyme solution added into 4 ml. of the reaction mixture (ml.) | Reduction ratio (%) | |
|---|---|---|
| | 5 minutes | 10 minutes |
| 0.01 | 5 | 10 |
| 0.10 | 16 | 34 |
| 0.20 | 37 | 73 |
| 0.40 | 58 | 98 |

EXAMPLE 3

The isolated H-402 strain was cultivated in the same manner as described in Example 1 and the obtained culture broth was separated by centrifuge. The resulting supernatant fluid was used as the broth enzyme solution. Besides, the supernatant fluid was further salted out by saturating with ammonium sulfate so as to be 60 % saturation. The resulting precipitate was dissolved in 0.05 M. phosphate buffer (pH7.5) and subjected to dialysis. To the solution was added acetone so as to be 40 % acetone. After removing the resultant precipitate, acetone was further added to the supernatant fluid so as to be 60 % acetone. The resultant precipitate was dissolved in the buffer solution above-mentioned and subjected to dialysis. To the resulting supernatant fluid was added 10 % aqueous calcium chloride solution and the precipitate was removed. The supernatant fluid was used as the purified enzyme solution.

Separately, cariogenic streptococcus (BHT) was cultivated in the same manner as described in Example 1. The obtained cells were freeze-dried and dispersed in distilled water to give a sample to be tested.

To 0.4 mk. of the sample to be tested were added 1.6 ml. of 0.025 M. acetate buffer (pH 6.0) and 2 ml. of the broth enzyme solution diluted to ten times by volume with distilled water or 2 ml. of the purified enzyme solution diluted to 500 times by volume with distilled water to give total 4.0 ml. The mixture was reacted at 37° C. for 30 minutes. The optical density of the reaction mixture at 600 m$\mu$ was measured and then the unit of the enzyme and the reduction ratio of the microorganisms to be lysed were calculated in accordance with the equation above-mentioned. The results are shown in Table IV.

TABLE IV

| | Unit/ml. | Reduction ratio (%) |
|---|---|---|
| Broth enzyme solution | 135 | 81 |
| Purified enzyme solution | 4000 | 48 |

EXAMPLE 4

The isolated H-402 strain was cultivated in the same manner as described in Example 1. By using the obtained enzyme solution, cell-lytic reaction was caried out on several kinds of microorganisms in the same manner as described in Example 1 and the unit was calculated. The results are shown in Table V.

TABLE V

| | Microorganisms to be lysed | Unit/ml. |
|---|---|---|
| (1) | Gram positive bacteria | |
| | Cariogenic streptococcus (BHT) | 95 |
| | Streptococcus salivarius | 90.7 |
| | Streptococcus lactis | 13.3 |
| | Streptococcus bovis | 17.1 |
| | Streptococcus faecalis | 105.5 |
| | Micrococcus lysodeikticus | 16.2 |
| | Sarcina lutea | 12.9 |
| | Staphylococcus albus | 34.2 |
| | Staphylococcus aureus | 25.7 |
| | Bacillus subtilis PCI 219 | 153.9 |
| | Bacillus sphaericus | 199.5 |
| | Bacillus megaterium | 28.0 |
| | Tetracoccus soyae | 12.9 |
| | Lactobacillus acidophilus | 36.8 |
| | Lactobacillus arabinosus | 73.6 |
| | Lactobacillus bulgaricus | 25.9 |
| | Lactobacillus casei | 8.6 |
| | Lactobacillus hiochi IFO 3077 | 20.1 |
| | Lactobacillus hiochi IFO 3078 | 31.6 |
| | Lactobacillus hiochi IFO 3079 | 20.1 |
| (2) | Gram negative bacteria | |
| | Escherichia coli | 3.8 |
| | Aeromonas hydrophila | 5.7 |
| | Arthrobacter simplex | 6.7 |
| | Proteus OM-9 | 2.2 |
| | Cellulomonas flavigena | 13.3 |
| | Flavobacterium esteroaromaticum | 16.7 |
| | Pseudomonas fluorescens | 17.1 |
| | Pseudomonas aeruginosa | 14.7 |

EXAMPLE 5

The isolated H-402 strain was cultivated in the same manner as described in Example 1 and the obtained culture broth was separated by centrifuge. The resulting supernatant fluid was salted out by 60 % saturation with ammonium sulfate. The resulting precipitate was dissolved in 0.05 M. phosphate buffer (pH 7.5) and subjected to dialysis. To the solution was added acetone so as to be 40 % acetone. After removing the resultant precipitate, acetone was further added to the supernatant fluid so as to be 60 % acetone. The resultant precipitate was dissolved in the buffer solution above-mentioned and subjected to dialysis. To the resulting supernatant fluid was added 10 % aqueous calcium chloride solution and the precipitate was removed. The supernatant fluid was freeze-dried to give an enzyme sample which activity was 544 units/mg. The enzyme sample was used in the following experiment.

Golden hamsters fed cariogenic diet (Krasse: Archives Oral Biology, Vol. 10, page 215, 1965), being 21 days old, were used in the experiment. After confirming no existance of streptomycin-resistant bacteria in the mouth, a streptomycin-resistant strain of cariogenic streptococcus (K-1-R) was introduced into cheek pouches of the hamsters. To one group of the hamsters was administered drinking water containing 7.5 units/ml. of the enzyme. About 10 ml. of the drinking water was drunk every day. To other group of the hamsters was administered drinking water containing no enzyme. About 10 ml. of the drinking water was drunk every day. Samples of dental plaques were collected by means of swab on some days after the infection.

The samples were dispersed into yeast extract solution and diluted optionally with distilled water. The solution was inoculated in Mitis salivarius agar medium containing streptomycin and cultivated at 37° C. for 40 hours, and then the formed colonies were counted. The results are shown in Tables VI and VII. In the Tables results of samples after 7 and 11 days are given, respectively.

TABLE VI

| Numbers of colonies ($\times 10^3$) | |
|---|---|
| Control (No added enzyme) | Added enzyme |
| 371 | 2 |
| 9 | 0 |
| 19 | 0 |
| 2 | <1 |
| 173 | 0 |
| 3 | <1 |
| 28 | 0 |

TABLE VII

| Numbers of colonies ($\times 10^3$) | |
|---|---|
| Control (No added enzyme) | Added enzyme |
| 151 | 0 |
| 81 | 0 |
| 14 | 0 |
| 21 | 1 |
| 25 | 3 |

EXAMPLE 6

The isolated B-1829 strain was inoculated on a slant agar medium containing 1 % of glucose, 0.2 % of peptone, 0.1 % of yeast extract, 0.1 % of meat extract and 1.5 % of agar and cultivated at 30° C. for 7 days. The obtained spores were inoculated into a 500 ml. Sakaguchi flask including 50 ml. of liquid medium (pH 7.5) containing 2 % of dextrin, 0.5 % of soybean powder, 0.25 % of peptone, 0.5 % of disodium hydrogen phosphate, 0.1 % of potassium dihydrogen phosphate 0.1 % of magnesium sulfate and 0.5 % of sodium chloride and subjected to shaking culture at 30 ° C. for 3 days. The obtained culture broth ws separated by filtration and the resulting filtrate was diluted with distilled water to give an enzyme solution of 20 times by volume on which the unit was calculated.

Separately, several kinds of cariogenic streptococcus to be lysed, each 3 – 4 platinum loops were inoculated into a 200 ml. flask including 190 ml. of liquid medium (pH 7.4) containing 2 % of glucose, 1 % of peptone, 1 % of meat extract, 0.5 % of sodium chloride, 0.2 % of yeast extract, 1 % of sodium acetate and 1 $\times$ 10$^{-4}$ M. manganese sulfate and subjected to stationary culture at 37° C. for 2 days. The produced cells were harvested by centrifuge, washed with water twice, centrifuged and freeze-dried.

To 0.4 ml. of a solution which was prepared by dissolving 100 mg. of the freeze-dried cells obtained above into 25 ml. of distilled water were added 2 ml. of the enzyme solution obtained above and 1.6 ml. of 0.025 M. tris buffer (pH 7.0) to give total 4 ml. The mixture was reacted at 37° C. for 5 minutes. The optical density of the reaction mixture at 600 mμ of a photoelectric colorimeter was measured and then the reduction ratio of the microorganisms to be lysed was calculated in accordance with the equation described above. The results are shown in Table VIII.

TABLE VIII

| Microorganisms to be lysed | Reduction ratio (%) 5 minutes | Unit/ml. |
|---|---|---|
| Cariogenic streptococcus (AHT) | 30 | 248 |
| Cariogenic streptococcus (BHT) | 54 | 452 |
| Cariogenic streptococcus (HSR-6) | 57 | 475 |
| Cariogenic streptococcus (HS-6) | 26 | 221 |
| Cariogenic streptococcus (K-1-R) | 31 | 262 |
| Cariogenic streptococcus (FA-1) | 45 | 379 |

EXAMPLE 7

The isolated B-1829 strain as cultivated in the same manner as described in Examle 6 to obtain an enzyme solution. On the other hand, intact cells of cariogenic streptococcus (BHT) were cultivated in the same manner as described in Example 6 to obtain freeze-dried cells which dissolved into distilled water to give a sample to be tested.

By using these enzyme solution and sample to be tested, the cell-lytic reaction was carried out in the same manner as described in Example 6 and the reduction ratio of the microorganisms to be lysed was calculated as well. The results are shown in TAble IX.

TABLE IX

| Volume of enzyme solution added into 4 ml. of the reaction mixture (ml.) | Reduction ratio (%) 5 minutes | 10 minutes |
|---|---|---|
| 0.01 | 6 | 12 |
| 0.10 | 29 | 55 |
| 0.20 | 37 | 73 |
| 0.40 | 58 | 98 |

EXAMPLE 8

The isolated B-1829 strain was cultivated in the same manner as described in Example 6. By using the obtained enzyme solution, the cell-lytic reaction was carried on the various microorganisms in the same manner as described in Example 6 and the unit was calculated. The results are shown in Table X.

TABLE X

| | Microorganisms to be lysed | Unit/ml. |
|---|---|---|
| (1) | Gram positive bacteria | |
| | Cariogenic streptococcus (BHT) | 455 |
| | Streptococcus salivarius | 272 |
| | Streptococcus lactis | 66 |
| | Streptococcus bovis | 456 |
| | Streptococcus faecalis | 40 |
| | Micrococcus lysodeikticus | 30 |
| | Sarcina lutea | 24 |
| | Sarcina marcescens | 4 |
| | Staphylococcus albus | 218 |
| | Staphylococcus aureus | 18 |
| | Bacillus subtilis | 1040 |
| | Bacillus sphericus | 784 |
| | Brevibacterium ammoniagenes | 50 |
| | Lactobacillus acidophilus | 36 |

TABLE X-continued

| | Microorganisms to be lysed | Unit/ml. |
|---|---|---|
| | Lactobacillus arabinosus | 116 |
| | Lactobacillus brevis | 500 |
| | Lactobacillus bulgaricus | 236 |
| | Lactobacillus casei | 60 |
| | Leuconostoc mesenteroides | 434 |
| | Tetracoccus soyae | 90 |
| (2) | Gram negative bacteria | |
| | Aerobacter aerogenes | 658 |
| | Aeromonas hydrophilia | 86 |
| | Acromobacter liquidum | 40 |
| | Alcaligenes faecalis | 68 |
| | Cellulomonas flavigena | 706 |
| | Escherichia coli | 40 |
| | Flavobacterium esteroaromaticum | 168 |
| | Pseudomonas fragi | 208 |
| | Pseudomonas aeruginosa | 56 |
| | Pseudomonas fluorescens | 56 |
| (3) | Other microorganisms | |
| | Mycobacterium phlei | 224 |
| | Candida albicans | 32 |
| | Saccharomyces cerevisiae | 60 |
| | Candida utilis | 16 |

EXAMPLE 9

The spores of the isolated B-1829 strain obtained in the same manner as described in Example 6 were inoculated into three 500 ml. Sakaguchi flasks including 50 ml. of liqud medium having the same composition as described in Example 6 and subjected to shaking culture at 30° C. for 24 hours.

To three 3 liters flasks including each 1 liter of the same medium as described above was inoculated each 50 ml. of the culture broth obtained above and then they were subjected to shaking culture at 30° C. for 24 hours. Thus obtained culture broths were used as a seed culture. The culture broths were inoculated into a 100 liters fermentation tank including 70 liters of the same medium as that in the above seed culture and subjected to submerged culture at 30° C., with an air pressure of 0.5 kg./cm², an aeration rate of 70 liters/min., an agitation velocity of 150 r.p.m. The unit of the obtained enzyme at each culture period are shown in Table XI.

TABLE XI

| Culture period (hour) | pH | Unit/ml. |
|---|---|---|
| 26 | 6.92 | 80 |
| 44 | 7.08 | 348 |
| 51 | 7.20 | 534 |
| 68 | 7.38 | 840 |

EXAMPLE 10

After 10 liters of the culture broth obtained by the same manner as described in Example 6 was separated by filtration, the filtrate was added onto 400 g. of cationic exchange resin Amberlite CG 50. The mixture was adjusted at pH 5.2 – 5.5 with concentrated aqueous ammonia, agitated under cooling for one hour and filtered. The adsorbed enzyme on the resin was eluted with ⅛ volume of 0.2 M. disodium hydrogen phosphate aqueous solution (pH 7.5). The eluate was salted out by 60 % saturation with ammonium sulfate (455 g. of ammonium sulfate per liter of eluate). The resulting precipitate was dissolved into 200 ml. of 0.05 M. phosphate buffer (pH 7.0) and dialyzed against 3 liters of the same buffer in cellophane tube for 24 hours to obtain 200 ml. of solution. To thus obtained solution was added 1/10 volume of diethylaminoethyl cellulose, and then the mixture was filtered and freeze-dried to give 2.5 g. of enzyme powder which activity was 400,000 units/g.

EXAMPLE 11

A toothpaste having the following prescription was prepared.

|  | (%) |
|---|---|
| Glycerin | 25.70 |
| Sodium carboxymethyl cellulose | 0.95 |
| Distilled water | 20.15 |
| Dicalcium phosphate | 46.00 |
| Calcium carbonate | 5.80 |
| Saccarin | 0.25 |
| Flavor | 0.65 |
| The broth enzyme solution obtained by Example 3 | 0.50 |
| Total | 100.00 |

EXAMPLE 12

A tooth powder having the following prescription was prepared.

|  | (%) |
|---|---|
| Sodium lauryl sulfate | 0.3 |
| Sodium carboxymethyl cellulose | 1 |
| Disodium hydrogen phosphate | 2 |
| Saccharin | 0.2 |
| Flavor | 1.8 |
| The enzyme sample obtained by Example 5 | 0.01 |
| Dicalcium phosphate | balance |

EXAMPLE 13

A dental liquid having the following prescription was prepared.

|  | (%) |
|---|---|
| Potassium lauryl sulfate | 0.3 |
| Ethyl alcohol | 8.0 |
| Saccharin | 0.3 |
| Flavor | 1.0 |
| The enzyme solution obtained by Example 6, not diluted | 0.3 |
| Distilled water | balance |

EXAMPLE 14

A chewable tablet having the following prescription was prepared.

|  | (%) |
|---|---|
| The enzyme solution obtained by Example 6, not diluted | 0.3 |
| Corn starch | 10 |
| Talc | 2 |
| Saccharin | 0.5 |
| Flavor | 0.2 |
| Sorbitol | balance |

EXAMPLE 15

Into 5 ml. of 0.01 M. phosphate buffer (pH Days) were dissolved 1 mg. of enzyme powder obtained by Example 10 and various stabilizers and the mixture was heated at 55°C. for one hour. On the resulting solution the activity of enzyme was measured to obtain a ratio of remaining activity of the enzyme. The results are shown in Table XII.

TABLE XII

| Stabilizer | | |
|---|---|---|
| Kind | Concentration (% by weight) | Remaining activity of enzyme (%) |
| Control | — | 15.7 |
| Sorbitol | 50 | 89.4 |
| Sorbitol | 70 | 94.8 |
| Mannose | 70 | 82.0 |
| Sucrose | 70 | 82.7 |
| Proline | 30 | 69.4 |
| Proline | 40 | 73.4 |
| Proline | 50 | 88.3 |
| Sorbose | 60 | 68.5 |
| Polyethylene glycol | 30 | 12.8 |
| Polyoxyethylene sorbitan monooleate (Tween 80) | 0.01 | 14.7 |
| Sorbitan monooleate (Span 80) | 0.01 | 11.5 |
| Maltose | 50 | 12.5 |
| Glucose | 70 | 35.7 |
| Glycerine | 20 | 17.1 |
| Mannitol | 10 | 25.7 |
| Soluble starch | 10 | 24.6 |
| Lactose | 10 | 21.6 |
| Xylose | 70 | 13.3 |
| Inositol | 10 | 25.0 |
| Glycine | 0.5 | 19.0 |
| Cysteine HCl | 0.5 | 15.3 |
| Sodium glutamate | 1 | 26.7 |

As made clear by the above results, at such severe condition, in the solutions of Control almost of the activity of enzyme was lost and on the contrary in the solutions containing the present stabilizers excepting soluble starch the enzyme was stably reserved (Soluble starch is not effective in aqueous solution but effective in solid state compositions).

EXAMPLE 16

Into 150 ml. of a 70 % by weight aqueous solution of sorbitol ws dissolved 150 mg. of enzyme powder obtained by Example 10 and the mixture was allowed to stand at 30° C. for one month. The change of the remaining activity of enzyme was observed. The results are shown in Table XIII.

TABLE XIII

| Days | Remaining activity of enzyme (%) | |
|---|---|---|
|  | Control | Sorbitol added |
| 0 | 100.0 | 100.0 |
| 7th | 22.5 | 99.6 |
| 14th | 11.1 | 88.1 |
| 21th | 7.8 | 76.7 |
| 30th | 7.2 | 71.6 |

EXAMPLE 17

In the same manner as described in Example 16, except that a 50 % by weight aqueous solution of proline was used instead of a 70 % by weight aqueous solution of sorbitol, there was tested the stabilizing effect of proline. The results are shown in Table XIV.

TABLE XIV

| | Remaining activity of enzyme (%) | |
|---|---|---|
|  | Control | Proline added |
| 0 | 100.0 | 100.0 |
| 7th | 23.4 | 100.0 |
| 14th | 13.2 | 94.1 |
| 21th | 8.5 | 82.2 |
| 30th | 7.8 | 76.9 |

EXAMPLE 18

Into 1 ml. of water was dissolved 15 mg. of enzyme powder obtained by Example 10 and further 20 mg. of sorbitol. The mixture was freeze-dried. After the product was allowed to stand at 30° C. for 3 months, the activity of enzyme was measured and then a lowering of the activity of enzyme was little found.

EXAMPLE 19

Into 1 ml. of water was dissolved 15 mg. of enzyme powder obtained by Example 10 and further 20 mg. of sucrose. The mixture was freeze-dried. After the product was allowed to stand at 30° C. for 3 months and the activity of enzyme was measured. The lowering of the activity of enzyme in the product was less than 10 %.

EXAMPLE 20

A freeze-dried product of 2 ml. of the enzyme solution obtained by Example 6, not diluted with water, 10 g. of sorbitol powder, 360 g. of disodium hydrogen phosphate ($Na_2HPO_4.12H_2O$), 140 g. of potassium dihydrogen phosphate ($KH_2PO_4$), 1 g. of saccharin and 0.5 g. of flavor were mixed to give a powdery mixture. The mixture may be diluted to 200 times with distilled water before the use and then applied into mouth.

EXAMPLES 21 – 25

Aqueous solutions of soluble starch having various concentration were prepared by dissolving soluble starch into water on heating and then cooling the mixture. Into 5 ml of each of the aqueous solutions prepared above were dissolved 60 mg. of enzyme powder. The mixtures were freeze-dried to give powders.

Thus obtained powders were allowed to stand at 40° C. for 9 days and then the remaining activity of enzyme was measured. The results are shown in Table XV.

TABLE XV

| Example No. | Concentration of soluble starch (mg./5 ml.) | Enzyme activity (unit/ml.) | | Remaining activity of enzyme (%) |
|---|---|---|---|---|
| | | Days 0 | 9th | |
| 21 | 400 | 270 | 252 | 93.3 |
| 22 | 300 | 340 | 220 | 64.7 |
| 23 | 200 | 283 | 160 | 58.7 |
| 24 | 100 | 253 | 80 | 31.6 |
| 25 | 50 | 138 | 19 | 13.8 |
| Control | — | 216 | 6 | 2.8 |

EXAMPLE 26

The powder obtained in the same manner as described in Example 21 and Control powder were allowed to stand at 30° C. for 6 months. And then the remaining activity of enzyme was measured. Although in Control powder the activity was lowered to 3.8 %, in the powder containing soluble starch almost 100 % of activity was remained.

EXAMPLE 27

To 2 ml. of water was added 130 mg. of soluble starch and the mixture was heated to dissolve the starch and then cooled. Into the aqueous starch solution were dissolved 20 mg. of freeze-dried enzyme obtained by Example 10 and the mixture was freeze-dried to give 150 mg. of a stabilized enzyme powder.

After being dissolved into 100 ml. of water, the powder obtained above can be used as a mouth wash.

EXAMPLE 28

In 1 ml. of each aqueous solution (concentration: 0, 0.5, 1.0 and 3.0 % by weigh) of sodium carboxymethyl cellulose (Celogen FSB (viscosity: 180 – 340 cps.) made by Daiichi Kogyo Seiyaku K.K.) was dissolved 15 mg. of the enzyme powder obtained by Example 10 and the mixture was freeze-dried to give a sodium carboxymethyl cellulose-enzyme powder. The powder was allowed to stand at 80° C. for 4 days and then measured the remaining activity of the enzyme. The results are shown in Table XVI.

Table XVI

| Concentration of aqueous sodium carboxymethyl cellulose solution (%) | Remaining activity of the enzyme* |
|---|---|
| 0 | 48.6 |
| 0.5 | 76.5 |
| 1.0 | 83.1 |
| 3.0 | 100.0 |

*Activity of original powder before allowed to stand at 80° C. = 100

EXAMPLE 29

To 1 g. of paste base consisting of 5.0 parts by weight of Plastibase 50 W, 0.83 part by weight of gelatine and 0.415 part of pectine was added the sodium carboxymethyl cellulose-enzyme powder obtained in the same manner as described in Example 28 so as to be 10 mg. of enzyme and the mixture was kneaded well to give a paste containing the enzyme. The paste was allowed to stand at 80° C. for 4 days and then calculated the remaining activity of the enzyme. The results are shown in Table XVII.

Table XVII

| Period for allowing to stand (hour) | Concentration of aqueous sodium carboxymethyl cellulose solution (%) | | |
|---|---|---|---|
| | 0.5 | 1.0 | 3.0 |
| 0 | 100.0 | 100.0 | 100.0 |
| 30 | 75.3 | 100.0 | 100.0 |
| 60 | 61.4 | 100.0 | 100.0 |
| 120 | 46.0 | 100.0 | 96.8 |
| 960 | 36.6 | 79.0 | 86.3 |

EXAMPLE 30

In 1 ml. of each aqueous solution of several concentrations of two kinds of sodium carboxymethyl cellulose (Terucello H (viscosity: 350 ± 40 cps.) and Terucello M (viscosity: 600 ± 50 cps.) made by Showa Jushi Kogyo K.K.) was dissolved 15 mg. of enzyme powder obtained in the same manner as described in Example 10 and the mixture was freeze-dried to give a sodium carboxymethyl cellulose-enzyme powder. The powder was allowed to stand at 80° C. for 15 hours and then measured the remaining activity of the enzyme. The results are shown in Table XVIII.

Table XVIII

| Sodium carboxymethyl cellulose | | Remaining activity of the enzyme (%) |
|---|---|---|
| Kind | Concentration | |
| — | — | 82.2 |
| Terucello H | 0.5 | 117.4 |
| | 1.0 | 108.4 |
| | 2.0 | 102.9 |

Table XVIII-continued

| Sodium carboxymethyl cellulose | | Remaining activity of the enzyme (%) |
|---|---|---|
| Kind | Concentration | |
| Terucello M | 0.5 | 95.6 |
| | 1.0 | 96.0 |
| | 2.0 | 95.5 |

EXAMPLE 31

In the same manner as described in Example 28, a sodium carboxymethyl cellulose-enzyme powder was obtained by using 1 ml. of 1 % aqueous solution of sodium carboxymethyl cellulose (Terucello M made by Showa Jushi Kogyo K.K.) and 15 mg. of enzyme powder obtained in the same manner as in Example 10. By using the sodium carboxymethyl cellulose-enzyme powder, a paste having the following prescription was prepared.

| | (mg.) |
|---|---|
| Plastibase 50 W | 91.0 |
| Hydroxyethyl cellulose | 9.0 |
| Sodium carboxymethyl cellulose-enzyme powder | 2.7 |
| α-Soluble starch | 0.3 |
| Magnesium sulfate | 5.0 |
| Sodium saccharin | 0.7 |
| Coloring agent | slight amount |
| Flavor | slight amount |

The paste thus obtained was very stable, and even when it was preserved at a room temperature for twelve months, the activity of the enzyme did not lower.

EXAMPLE 32

In the same manner as described in Example 28, a sodium carboxymethyl cellulose-enzyme powder was obtained by using 1 ml. of 3 % aqueous solution of sodium carboxymethyl cellulose (Celogen FSB made by Daiichi Kogyo Seiyaku K.K.) and 15 mg. of the enzyme powder obtained in the same manner as in Example 10. By using the sodium carboxymethyl cellulose-enzyme powder, a troche having the following prescription was prepared.

| | (mg.) |
|---|---|
| Mannitol | 278.2 |
| Sodium carboxymethyl cellulose | 10.0 |
| Sodium carboxymethyl cellulose-enzyme powder | 3.0 |
| Magnesium sulfate | 5.0 |
| Magnesium stearate | 1.5 |
| Sodium saccharin | 0.3 |
| Flavor | slight amount |

The troche thus obtained was very stable, and when it was preserved at a room temperature for 12 months, the activity of the enzyme did not lower.

EXAMPLE 33

By using a sodium carboxymethyl cellulose-enzyme powder obtained in the same manner as described in Example 31, an effervescent granule having the following prescription was prepared.

| | (mg.) |
|---|---|
| Tartaric acid | 125 |
| Sodium hydrogen carbonate | 188 |
| Magnesium sulfate | 12 |
| Mannitol | 412 |
| Lactose | 250 |
| Sodium saccharin | 5 |
| Levo-menthol | 5 |
| Sodium carboxymethyl cellulose-enzyme powder | 3.7 |

When the effervescent granule thus obtained was preserved at a room temperatue for 12 months, the activity of the enzyme did not lower. The granule is dissolved in about 200 ml. of water when used and then it is used as a mouth wash.

What is claimed is:

1. A composition for preventing and treating dental caries comprising
   a conventional oral hygiene carrier, particularly including water or mouth wash, chewing gum or troche, tooth powder, toothpaste or ointment, said carrier containing as an essential active ingredient
   an enzyme capable of lysing cells of dental caries-inducing microorganisms which is produced by cultivating a Streptomyces microorganism selected from the group consisting of *Streptomyces diastatochromogenes* (ATCC 21481), *Streptomyces farinosus* (ATCC 21482), *Streptomyces globisporus* (ATCC 21553) and *Streptomyces griseus* Var. H-402 (ATCC 21483) and mutants thereof and recovering the produced enzyme from the culture broth, said enzyme being contained in a dose unit of an effective amount of from 1 to 5,000 units, one unit of activity being defined as that amount of enzyme giving an initial linear decrease in optical density of 0.001 per minute of the reduction ratio of said bacteria cells, in turbidity, when the optical density of the reaction mixture of said cells, in lytic reaction with said enzyme, is measured at 600 m$\mu$ of a photoelectric colorimeter.

2. A method for preventing and treating dental caries which comprises washing or rinsing the mouth with water containing 0.1 to 50 units per milliliter of the enzyme in accordance with claim 1.

3. A method for preventing and treating dental caries which comprises holding in the mouth a troche containing 1 to 5,000 units of the enzyme in accordance with claim 1.

4. A method for preventing and treating dental caries which comprises brushing teeth with finger or a toothbrush spread with toothpaste or tooth powder containing 1 to 5,000 units per gram of the enzyme in accordance with claim 1.

5. A method for preventing and treating dental caries which comprises rubbing teeth with an ointment containing 1 to 5,000 units per gram of the enzyme in accordance with claim 1.

6. The composition as set forth in claim 1 in the form of chewable tablet or troche containing 1 to 5,000 units of the enzyme.

* * * * *